United States Patent [19]

Huc et al.

[11] Patent Number: 5,244,672

[45] Date of Patent: Sep. 14, 1993

[54] COMPOSITION CONTAINING LIPOSOMES STABILIZED BY A STABILIZING SUPPORT BASED ON ATELOCOLLAGEN AND GLYCOSAMINOGLYCANS

[75] Inventors: Alain Huc, Sainte Foy les Lyon; Chantal Buffevant, Vernaison; Daniel Herbage, Lyons, all of France

[73] Assignee: Coletica, Lyons, France

[21] Appl. No.: 788,481

[22] Filed: Nov. 6, 1991

Related U.S. Application Data

[63] Continuation-in-part of Ser. No. 537,379, Jun. 13, 1990, abandoned, which is a continuation-in-part of Ser. No. 362,079, Jun. 6, 1989, abandoned, which is a continuation-in-part of Ser. No. 284,126, Dec. 14, 1988, abandoned.

[30] Foreign Application Priority Data

Apr. 11, 1989 [FR] France .................. 89 04762

[51] Int. Cl.$^5$ ............................................. A61K 9/127

[52] U.S. Cl. .................. 424/450; 424/401; 264/4.1; 264/4.3; 428/402.2; 514/21; 514/56; 514/62

[58] Field of Search ............... 424/450, 401; 264/4.1, 264/4.3; 428/402.2; 514/21, 56, 62; 530/356

[56] References Cited

U.S. PATENT DOCUMENTS 4,108,849 8/1978 Thomas ..................... 424/95
4,670,185 6/1987 Fujiwara et al. ............ 264/4.1

Primary Examiner—Thurman K. Page
Assistant Examiner—G. S. Kishore
Attorney, Agent, or Firm—Weingarten, Schurgin, Gagnebin & Hayes

[57] ABSTRACT

The invention relates to a composition containing liposomes, stabilized by a stabilizing support comprising a mixture of atelocollagen and glycosaminoglycans in a relative proportion preferably ranging between 18 and 25% by weight of the atelocollagen. The preferred use of this composition is in pharmacy or beauty care.

28 Claims, 2 Drawing Sheets

COMPOSITION CONTAINING LIPOSOMES STABILIZED BY A STABILIZING SUPPORT BASED ON ATELOCOLLAGEN AND GLYCOSAMINOGLYCANS

This is a continuation-in-part application of Ser. No. 07/537,379 filed on Jun. 13, 1990, now abandoned, which is a continuation-in-part application of Ser. No. 07/362,079 filed Jun. 6, 1989, now abandoned, which is a continuation-in-part application of Ser. No. 07/284,126 filed Dec. 14, 1988, now abandoned.

The present invention relates essentially to a stabilization process for hydrated lipid lamellar phases, for example liposomes, a composition of hydrated lipid lamellar phases, for example liposomes, stabilized by the use of a stabilizing support based on atelocollagen and glycosaminoglycans, and its utilization in pharmacy and in beauty care.

Hydrated lipid lamellar phases, a special form of which is constituted by liposomes, have been known since the work of BANGHAM (see BANGHAM et al., Journal of Molecular Biology, 13: 238; 253 (1965) and in BANGHAM et al., Chem. Phys. Lipids, 1: 255 (1967)). Many other articles have been published on liposomes (see PAPAHADJOPOULOS, Biochem, Biophys. Acta, 135 (1967), pages 624–638 and WEISSMANN in Journal of Lipids Research, volume 9, (1968), pages 310 to 318).

It is known that the liposomes, which are phospholipid capsules, are becoming more and more important in beauty care and pharmacy because they enable active substances to be transported towards the cells by which they are absorbed. In fact, and this has been known since the work of BANGHAM, since the phospholipid nature of their membrane is very similar to that of the cells, it leads to fusion of the two envelopes.

Unfortunately, liposomes have such low stability that their development has been seriously slowed down, a circumstance which constitutes a major problem. In many cases, the reservoirs constituting the liposomes break down before entering into contact with the target cells. Furthermore, their integration into a finished product quite often causes the destruction of the reservoirs. In particular, in beauty care, the production of an emulsion containing liposomes is an extremely delicate undertaking, since the fat phase can cause opening of the phospholipid membrane. Much work has also been devoted to the stabilization of liposomes by substances which, in addition, must be biocompatible Various solutions have been suggested for the stabilization of liposomes, in particular the utilization of a gel form in a hydrocolloid (C.A., volume 97, 1982, 188 156K referring to an article published in J. Pharm. Pharmacol., 1982, 34 (7, 473-4); see also the document WO 85/03640, in which a large number of substances are described which can be used as gelling agents, in particular carbohydrates such as the celluloses, gums in particular carrageenin, xanthan, collagen, polyacrylamide, polysiloxanes, polymers of aminoacids such as gelatinized albumin, gelatin (page 12, lines 23 to 34).

The utilization of a gel presents many disadvantages. First of all, it seriously complicates the preparation of the compositions, in particular pharmaceutical or cosmetic compositions. In fact, the utilization of a gel poses serious handling problems on account of the physical properties of the gel, and in particular their non-pourable character. Finally, a problem relating more particularly to the use of collagen as gel support is that collagen exhibits a certain antigenicity, even though it is low. Again in the case of collagen, acid-soluble collagen is usually used. Now the composition must have a pH close to neutrality from the point of view of the stability of the liposomes as well as one close to the physiological pH in the case when it is used in beauty care, but these are pH conditions under which the acid-soluble collagen precipitates and the inclusion of liposomes becomes impossible. This phenomenon can be prevented by very complicated and expensive conditions which cannot be applied on an industrial scale and which include conditions of low temperature close to 4° C. This means that industrial production at low cost cannot be contemplated.

Thus, the aim of the present invention is to resolve the new technical problem consisting of providing a solution which makes it possible to stabilize the hydrated lipid lamellar phases, in particular liposomes, with the aid of a stabilizing support which is available in the form of a sufficiently fluid solution to eliminate all of the disadvantages inherent in the use of stabilizing supports in the form of a gel.

Another aim of the present invention is to resolve the new technical problem consisting of supplying a solution which makes it possible to stabilize the hydrated lipid lamellar phases, in particular liposomes, by the use of a sufficiently fluid stabilizing support which is devoid of antigenicity and which, in addition, requires only the implementation of an extremely simple procedure, applicable industrially under simple operating conditions, and which can be varied relatively widely to give rise to a practically perfect reproducibility.

Another aim of the present invention is to resolve the new technical problem consisting of providing a solution which enables the hydrated lipid lamellar phases, in particular liposomes, to be stabilized by the use of a stabilizing support compatible with the formation of emulsions.

All of these technical problems are resolved for the first time by the present invention in a satisfactory manner which can be used industrially.

Thus, from one point of view, the present invention provides a stabilization process for stabilizing hydrated lipid lamellar phases, for example vesicles of the liposome type comprising mixing said hydrated liqid lamellar phase with a stabilizing support, comprising a substantially homogeneous solution containing atelocollagen and glycosaminoglycans.

According to a particularly advantageous embodiment, the relative weight ratio of glycosaminoglycans with respect to the atelocollagen ranges between 10 and 70 percent.

A more advantageous relative weight ratio of glycosaminoglycans with respect to the atelocollagen ranges between 15 and 50 percent.

The relative proportion of glycosaminoglycans with respect to the atelocollagen lies preferably between 18 and 25% by weight of the atelocollagen.

According to another particular embodiment of the invention, the relative weight ratio between atelocollagen and the lipids of the hydrated lipidic lamellar phases, for example liposomes ranges between 10 and 100 percent.

According to one embodiment, said stabilizing support is prepared in the following manner:
    a) a solution of atelocollagen and a solution of glycosaminoglycans are prepared separately; then b) the said solution of atelocollagen is mixed with the solution of glycosaminoglycans.

According to a further embodiment of the invention, said stabilization process comprises preparing the hydrated lipid lamellar phases, for example vesicles of the liposome type, in the presence of a homogeneous solution of atelocollagen and of glycosaminoglycans.

According to one variant of the embodiment of the process according to the invention, the homogeneous mixture is prepared by introducing the solution of glycosaminoglycans into the solution of atelocollagen.

According to a particular embodiment of the invention, the solution of glycosaminoglycans is prepared by dissolving the glycosaminoglycan in a basic aqueous solution, the pH of which is adjusted so that after mixing with the solution of atelocollagen, the pH of the mixture constituting the stabilizing support remains slightly basic while being close to neutrality. Preferably, the final pH is close to 8.

According to a particularly advantageous feature, this basic aqueous solution is an aqueous solution of sodium hydroxide.

According to another advantageous feature, the concentration of glycosaminoglycan in the solution of glycosaminoglycans varies from 0.5 to 4%, and more especially from 0.5 to 2% and preferably is close to 1%.

According to another feature of the process of the invention, the solution of atelocollagen is an aqueous solution of atelocollagen, preferably having a concentration varying between 0.5 and 2% by weight, and more preferably close to 1%. This solution of atelocollagen can be prepared according to the invention by the dissolution of fibres of atelocollagen in a slightly acidic aqueous solution.

According to a particular embodiment of the invention, these fibres of atelocollagen are dissolved in 0.1M acetic acid.

According to another particular embodiment of the process according to the invention, the atelocollagen is produced by enzymatic digestion of collagen.

According to another special feature of the process according to the invention, the hydrated lipid lamellar phases, for example liposomes, are introduced into the solution of the stabilizing support according to the invention, the volumes of the two components being approximately equal.

According to another particular embodiment of the invention, the proportion of the lipid lamellar phases, for example liposomes, represents about 1% of the final composition.

According to a further variant of embodiment, the hydrated lipid lamellar phases, and particularly the vesicles of the liposome type are encapusulating at least a part of an active ingredient. This active ingredient can be added to the solution of atelocollagen and glycosaminoglycans. Any ingredient can be used. Preferred active ingredients are cosmetic or pharmaceutical active ingredients, for example heparan sulfate may be used as active ingredient.

According to a second feature, the present invention also provides a composition containing hydrated lipid lamellar phases, for example vesicles of the liposome type, stabilized by a stabilizing support comprising a substantially homogeneous solution containing atelocollagen and glycosaminoglycans.

According to a variant said hydrated lipid phases have been prepared in the presence of said stabilizing support.

According to a variant of a particular embodiment of the invention, the glycosaminoglycans used are chosen from among the structural glycosaminoglycans, in particular hyaluronic acid, chondroitin 4-sulfate, chondroitin 6-sulfate, dermatan sulfate, heparan sulfate, keratan sulfate; all the secretory glycosaminoglycans, in particular heparin and its derivatives as well as the mucoitin sulfates.

According to another feature of the composition according to the invention, this latter relates to the starting solutions of atelocollagen and glycosaminoglycans for the preparation of the solution of the mixture, the properties of which have been set out previously in the process.

According to another feature of the composition according to the invention, the solution of the stabilizing support has a pH which is slightly basic but close to neutrality, and is preferably of the order of 8.

According to another feature of the composition according to the invention, this composition is produced by mixing approximately equal volumes of solutions of hydrated lipid lamellar phases, for example liposomes, and solutions of the stabilizing support.

A preferred utilization of the compositions according to the invention relates to a utilization in pharmacy or beauty care, in the form of pharmaceutically or cosmetic compositions. For this purpose, the composition may be used as such or after the addition of various components or appropriate excipients well known to the person skilled in the art without any special problem, provided it is established that this addition does not modify the stability of the hydrated lipid lamellar phases, in particular liposomes.

In a totally unexpected manner, the invention leads to a diminution of the antigenicity of the stabilizing support.

In addition, the preparation provides a marked improvement in the proportion of one of the components of the stabilizing support, namely the atelocollagen towards collagenases which leads to a prolongation "in vivo" of the retarding effect of atelocollagen.

This stabilizing support exhibits an enhanced hydrating capacity and shows a more marked regenerative action on the dermis and the epidermis by increase of cellular development.

Another particularly unexpected advantage and one of decisive importance from the point of view of industrial exploitation lies in the fact that the atelocollagen used in the form of a solution according to the present invention is mixed in an extremely simple manner with the glycosaminoglycans, thus leading to a simplification of the stabilization process and hence of the process for the manufacture of the compositions, whether for therapeutic or cosmetic use. This support is compatible with the formation of emulsions.

Furthermore, the use of a stabilizing support in the form of a solution gives rise to a very advantageous pourable character as will be readily appreciated by the person skilled in the art.

It can thus be seen that the invention provides decisive and remarkable improvements compared with the prior art.

Other aims, properties and advantages of the invention will also become clearly apparent in the light of the explanatory description which follows and which makes reference to several examples of the preparation of compositions according to the invention by implementing the process according to the invention described earlier, said description taken in light of the accompanying drawings in which:

FIG. 1 shows the influence of COLL-CAG on the permeability of liposomes with regard to time; and FIG. 2 shows the permeability of liposomes with regard to time in the presence and absence of COLL-GAG.

DESCRIPTION OF THE PREFERRED EMBODIMENT

Example 1

Figure 1:
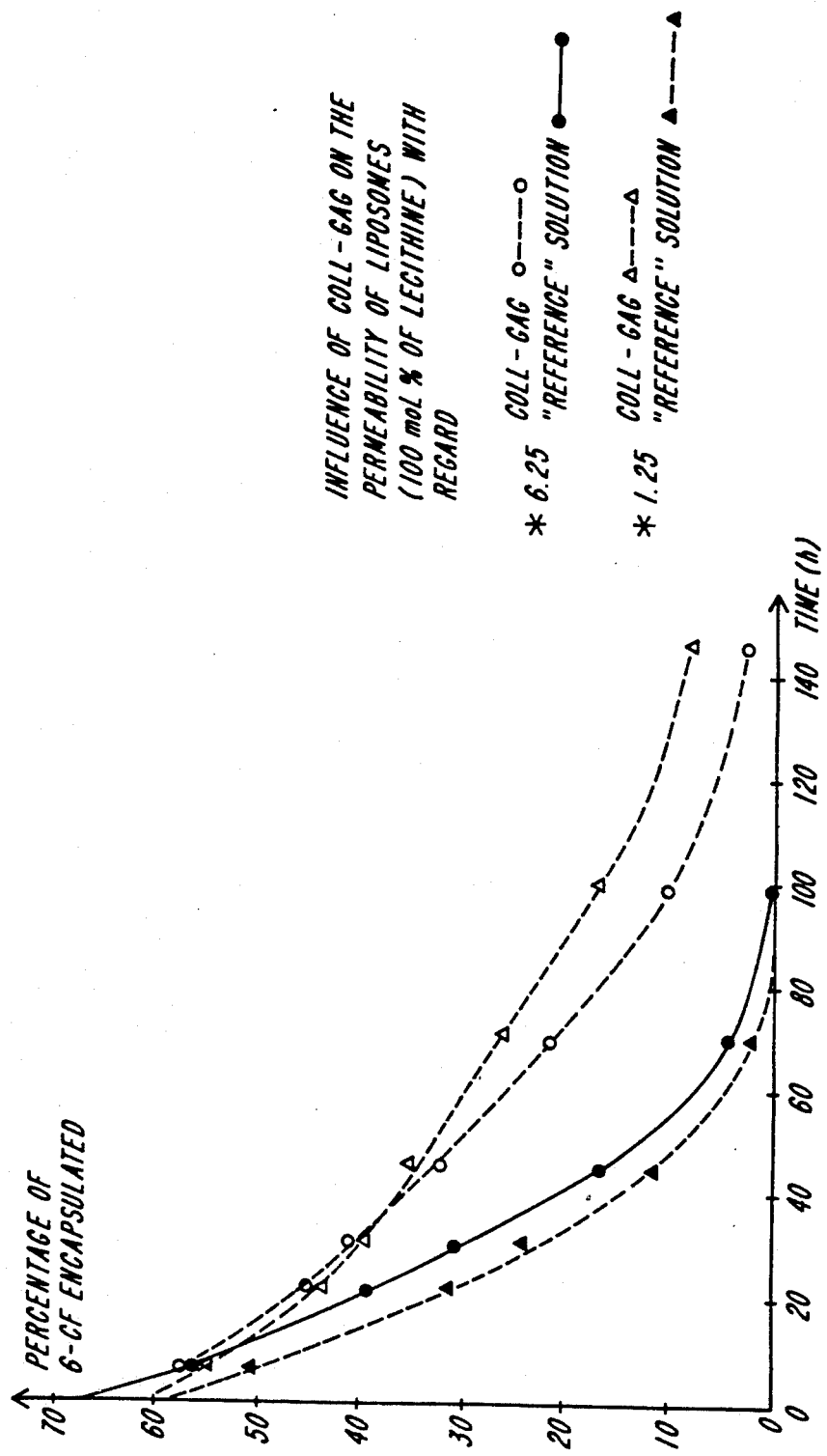

Preparation of a Liposomal Composition Within an Atelocollagenglycosaminoglycan Support a) Preparation of large multilamellar vesicles (M.L.V.)

Soy-bean lecithin is dissolved in chloroform and then deposited in the form of a thin film on the walls of a glass flask by evaporation of the solvent in a vacuum. Water heated to 80° is then poured into the flask and maintained at this temperature for 10 minutes while being stirred with a Vortex mixer. The volume of water used is such that the final mixture contains 1% of lecithin. The contents of the flask are then left to cool to room temperature. The solution thus contains 1% of phospholipid in the form of MLV liposomes.

If a water-soluble substance is to be encapsulated, it should be dissolved in the water added during the preparation. In the case in which a lipophilic substance is to be introduced into the membrane, it should be incorporated into the chloroform phase containing the phospholipid.

b) Preparation of uncross-linked collagen or atelocollagen

The skin of freshly slaughtered calves is subjected to a chemical treatment for the removal of hair in a bath containing 3% of sodium sulfide and 4% of lime, the proportion being 100 g of skin for 200 cm$^3$ of solution. The dermis is then isolated from the rest of the skin by a stripping operation using a rotating band saw.

The tissue obtained is ground and extruded through a grid containing 4 mm holes. The ground preparation is then placed in contact with saturated lime water in the proportions of 1 kg for 4 l of solution for 3 weeks. The skin thus treated is separated from the supernatant by continuous centrifugation at an acceleration of 2000 g in a centrifuge rotating at 4000 rev/min. The pellet is then washed twice with tap water with gentle stirring in a stainless steel tank at a dilution of 1 kg of pellet per 4 l of water. The ground preparation is then subjected to two treatments with phosphate buffer pH 7.8 (21.7 g/l of Na$_2$HPO$_4$ and 0.78 g/l of KH$_2$PO$_4$) under the same conditions as those for the water washings. The pellet is then washed in two baths of deionized and sterile water. The ground preparation obtained is placed in a solution of acetic acid (0.5 g/l, pH 3.4) at a dilution of 1 kg for 20 l of solution. After being stirred for 5 minutes, the supernatant is separated from the pellet by continuous decantation according to the previously described technique. The atelocollagen is then precipitated from the supernatant by the addition of dry sodium chloride to give a final concentration of about 10%. After decantation of the supernatant under gravity, the fibres obtained are dialyzed against deionized and sterile water with the aid of dialysis membranes, preferably made from dialysis tubing, the cut-off point of which lies between 6000 and 8000 daltons. After a check has been made by means of silver nitrate that the dialyzed fibres no longer contain sodium chloride, they are dissolved in a bath containing 6 g/l of acetic acid so as to give a final concentration of 1% of atelocollagen. The mixture is stirred gently for 24 hours.

c) Preparation of chondroitin 4-sulfate

Calf nasal septa, from which muscle and adipose tissue have been removed, are minced and ground by extrusion through a grid containing 4 mm holes; the mince is then placed for 24 hours at a temperature of 6° C. in potassium chloride buffer (11.8 g/l of KCL, 78.8 mg/l of cysteine, EDTA 180 mg/l) containing 1% "MERCK" papain in the proportion of 130 g of mince for 1 l of buffer.

The supernatant is separated from the pellet by continuous centrifugation using a centrifuge rotating at 400 rev/min. 40 g/l of trichloroacetic acid are then added to the supernatant. The precipitate is removed by continuous centrifugation using the technique just described. The supernatant is neutralized with sodium hydroxide pellets. The mixture is then dialyzed against deionized and sterile water with the aid of dialysis tubing, the cut-off point of which lies between 6000 and 8000 daltons. The dialyzed solution is lyophilized. Chondroitin 4-sulfate is obtained in the dry state.

d) Preparation of the atelocollagen-chondroitin 4-sulfate mixture

The mucopolysaccharide is dissolved in a bath containing sodium hydroxide to give a 1% solution. This solution is added to a gently stirred solution of atelocollagen containing 1% of protein and in the proportion of 250 ml of solution for 1 l of atelocollagen solution. The amount of sodium hydroxide is such that the final pH is 8.

e) Preparation of the composition liposomes-atelocollagen-chondroitin 4-sulfate

The aqueous solution of liposomes containing 2% of soy-bean lecithin is introduced into the gently stirred mixture of atelocollagen-chondroitin 4-sulfate, the volumes of the two solutions being equal so that the final complex contains 1% of lecithin.

Example 2

Preparation of a Liposome Composition in an Atelocollagen-Glycosaminoglycan Support a) Preparation of SUV liposomes (small unilamellar vesicles)

Egg white lecithin is dissolved in ethanol at a concentration of 30 mmol/l. The alcoholic solution is then added to 0.15M solution of potassium chloride. Unilamellar vesicles then form. The suspension is then dialyzed to remove the residual alcohol and may be concentrated to 2% by ultrafiltration.

b) preparation of uncross-linked collagen or atelocollagen

The mince of calf skin is prepared in the same manner as in the preceding example. The mince is then subjected to two treatments with phosphate buffer pH 7.3 (21.7 g/l of Na$_2$HPO$_4$ and 0.79 g/l of KH$_2$PO$_4$). The treatment is conducted at a concentration of 1 kg of mince per 1 l of solution. After each treatment, the residue is recovered by continuous centrifugation using a centrifuge rotating at 4000 rev/min. and giving rise to an acceleration of 2000 g. After washing with phosphate buffer, the mince is washed in two baths of deionized and sterile water under the same conditions as those used previously.

The mince is then placed at a concentration of 200 g/l in a solution of 0.01N hydrochloric acid containing 7.5% of pepsin with respect to the collagen. The mixture is left to stand for 24 hours at ambient temperature. After this lapse of time, the same quantity of pepsin is again added to the bath and the mixture is left to stand under the same conditions as those previously described.

The supernatant is separated from the pellet by continuous centrifugation by means of the technique previously described. Sodium chloride is added to the supernatant to give a concentration of 10%. The atelocollagen fibres are isolated by means of continuous centrifugation and placed in Visking dialysis tubes (ref. 30/32). After complete removal of the sodium chloride, the fibers are dissolved in 0.1M acetic acid so as to give a concentration of atelocollagen of 1%.

c) Preparation of dermatan sulfate

Pig skin, stripped in a standard manner of the corneous layer and subcutaneous tissues, is minced and ground by extrusion through a grid containing 4 mm holes.

The mince is then washed with a chloroform-methanol mixture (in the proportion of 2/1 by volume). After evaporation of the solvent in a vacuum, the dry residue is treated in the same way as the mince obtained from the nasal septa in example, and dermatan sulfate is obtained in the dry state.

d) Preparation of the atelocollagen-dermatan sulfate mixture

The mucopolysaccharide is dissolved in a bath containing sodium hydroxide to give a 1% solution. This solution is added to a gently stirred solution of atelocollagen containing 1% of atelocollagen and in the proportion of 300 ml of solution for 1 l of atelocollagen solution. The amount of sodium hydroxide is such that the final pH is 8.

e) Preparation of the liposome-atelocollagen-dermatan sulfate complex

The aqueous solution of liposomes containing 2% of egg white lecithin is introduced into the atelocollagen-dermatan sulfate mixture with gentle stirring. Since the volume of the collagen and the liposome solutions are equal, the final complex contains 1% of lecithin.

EXAMPLE 3

Control Assay of the Stability of the Liposomes in Their Atelocollagenglycosaminoclycan Support According to the Invention Examples 1 and 2

The control of the presence and quality of the liposomes is carried out by electron microscopy. For that, the preparations prepared in conformity with examples 1 and 2 and containing 1% of lecithin are diluted 10 fold. One drop of the diluted solution is placed on an electron microscope grid coated with an appropriate film, for example a film of Formavar ®. Immediately afterwards, a drop of a 2% by weight solution of phosphotungstic acid, freshly prepared and neutralized to pH 7, is added to the same grid. The grid is allowed to dry in air and examined by transmission microscopy.

The electron microscopy control shows that the liposomes maintain their shape and that they may be placed in contact with water without difficulty. The lyophilization step makes it possible, on the one hand, to preserve the complex for an unlimited period and, on the other hand, to prepare very concentrated pastes of liposomes and atelocollagen which can be injected into the organism in a very small volume.

The stability of liposomes in the compositions according to the invention is checked by subjecting these compositions to an ultrasonic shock.

For that, the composition may be agitated with a homogenizer of the "Ultra-Turax" type rotating at 22,000 rev/min for times of 1,3 and 5 minutes.

A comparison is carried out by subjecting an aqueous solution of the liposomes along to the same conditions.

The electron microscopy of the compositions thus treated, namely the compositions according to the invention obtained in examples 1 and 2 and the comparative composition composed of an aqueous solution of the liposomes alone, brings out the fact that in aqueous solution the liposomes progressively disintegrate to give rise to disorganized membranes. On the other hand, the liposome vesicles maintain their shape within the stabilizing supports according to the invention even after treatment for 6 minutes.

The invention thus makes it possible to stabilize the liposomes while conserving the advantage inherent in the use of a solution of high fluidity, as stated earlier.

Example 4

Preparation of a Composition of Liposomes Containing Hepara Sulfate as Active Ingredient in the Presence of a Complex Solution of Atelocollagen-Glycosaminoglycans 10 kg of atelocollagen-glycosaminoglycan complex, containing 20 g of collagen, 5 g of chondroitin 4-sulfate are prepared as described in steps b to d of Example 1 above. To this solution may be added conserving agents, for example 10 g of Nipagin ® (the soda salt of methyl paraben or the soda salt of methyl parahydroxybenzoate) and 50 g of Phenonip ® (methyl paraben 16%; ethyl paraben 4%; propyl paraben 2%; butyl paraben 6%; 2-phenoxyethanol 72%), manufactured by NIPA Laboratories Limited (UK). In this solution are added 10 g of heparan sulfate with mechanical stirring until a homogeneous solution is obtained. The pH is adjusted to 7.2 with sodium hydroxide.

In this bath maintained with stirring at ambient temperature, 100 g of egg white lecithin are added. After complete dissolution, the mixture is agitated by an ultrasonic stirrer of the Ultra-Turax UTL 60 type, rotating at 8000 rpm for 10 mins.

10 kg of solution containing stabilized liposome vesicles in the atelocollagen glycosaminoglycan solution are thus obtained.

The stability of the liposomes is checked by electronic transmission microscope as described in Example 5.

Example 5

Stability of the Liposomes Obtained in Example 4

The stability of the liposomes obtained in Example 4 is checked by studying the permeability of the membrane of the liposomic vesicles with respect to 6-carboxyfluorescein (6-CF).

To that end, the 6-carboxyfluorescein which has been added in the atelocollagen-glycosaminglycan solution, is encapsulated in the liposomic vesicles.

Liposomes encapsulating the 6-carboxyfluorescein were firstly prepared in conventional manner by ultrasonic agitation, the liposomes obtained therefore being non-stabilized, called "control" solution, FIG. 1, in which is introduced a volume of dilution identical to the volume of stabilizing/atelocollagen-glycosaminoglycan support, abbreviated to COLL-CAG, having the same pH and the same osmotic pressure, the "control" solution curve being made for two different values of the lipid concentration atelocollagen concentration ratio, equal respectively to 6.25 ("control solution curve ○—○) or to 1.25, curve Δ—Δ, FIG. 1, with respect to lipsomes prepared by ultrasonic agitation in conventional manner but stabilized thereafter by the introduction of the latter in an atelocollagen-glycosaminoglycan solution (cf. curves COLL-GAG ○—○Δ—Δ, FIG. 1).

Figure 2:
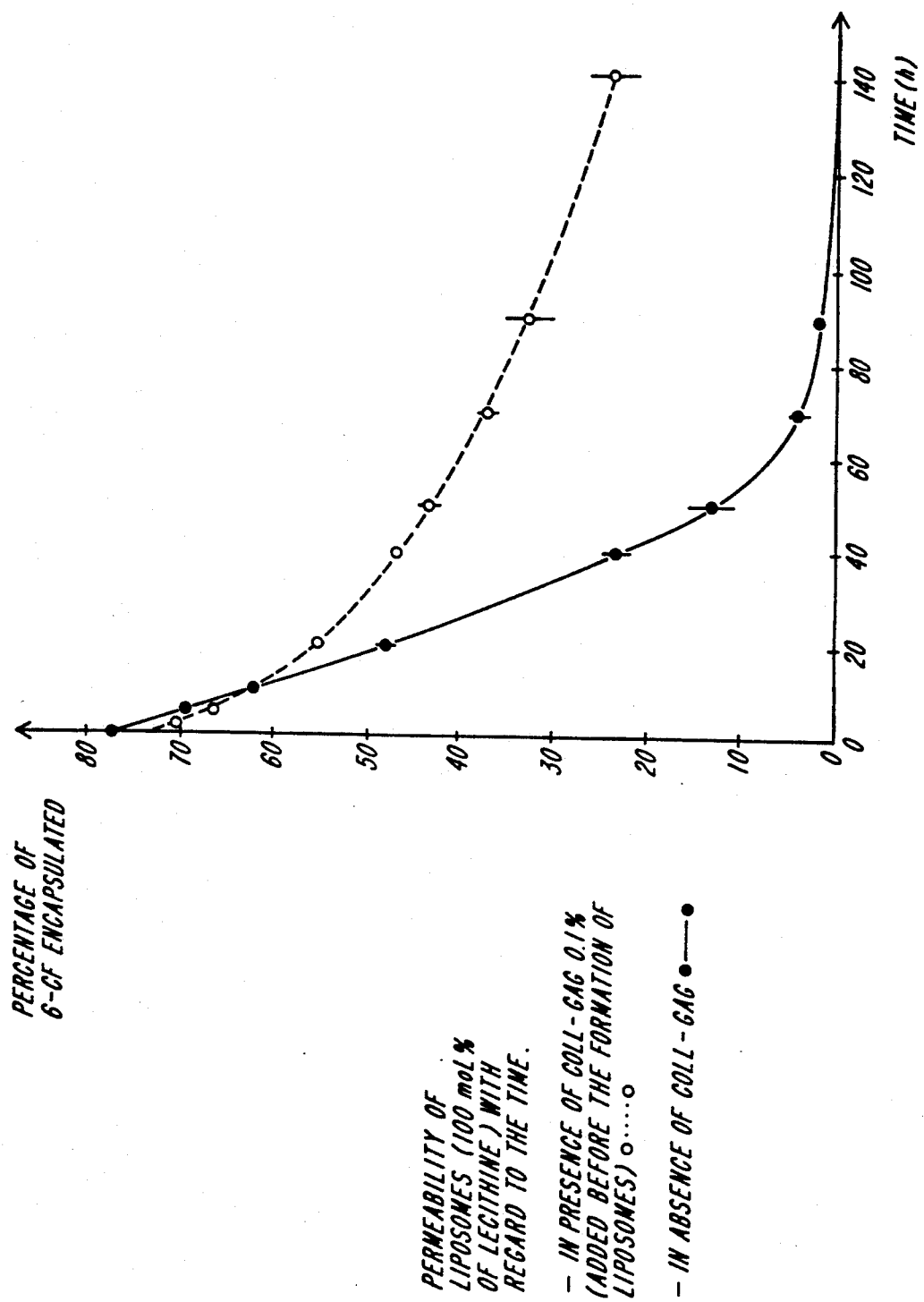

Furthermore, FIG. 2 shows the curves of permeability of the liposomes (100 mol of lecithin) in the course of time, viz. when the liposomes are prepared in the presence of the 0.1% atelocollagenglycosaminoglycan solution according to the present invention (curve ○—○, FIG. 2) with respect to the "control" solution (in the absence of COLL-GAG) curve ○—○, FIG. 2).

An examination of FIGS. 1 and 2 very clearly shows that the permeability of the liposomic wall is reduced in the case of the liposomes stabilized by the solution of atelocollagen-GAG after formation of the capsules with respect to the non-stabilized liposomes (cf. FIG. 1). This phenomenon is marked still more when liposomes have been formed in the presence of atelocollagen-GAG (FIG. 2).

Example 6

Pharmaceutical or Cosmetic Composition

A composition prepared as in examples 1 and 2 can be used as a pharmaceutical or cosmetic composition. Quite naturally, in such a case it is usually necessary to encapsulate an active ingredient in the liposomes, either in the membrane of the liposome or in the interior of the liposomes depending on whether the active substance is hydrophobic or hydrophilic in nature, according to the procedure which is, moreover, cited in example 1 at the end of paragraph a) and is well known to the person skilled in the art.

Various excipients or other active components may be added as desired, provided that they do not destroy the stabilizing effect of the support according to the invention, as can be readily understood.

Example of a Composition in an Emulsified Form

This composition has the following empirical formulation, the percentages being expressed by weight:

|  | % by weight |
|---|---|
| Polyoxypropylene 15 (POP) - Stearyl alcohol | 4 |
| Sodium 2-stearoyl lactate | 4 |
| Polyoxy ethylene fatty acid ester | 3 |
| Glycerol stearate | 1 |
| Dioctonate of polypropylene glycol 2 | |
| Glycerol stearate | 2 |
| Methyl parabenzoate | 0.3 |
| Polypropylene glycol | 2 |
| Allatoin | 0.2 |
| Carboner 940 ® | 0.2 |
| Triethanolamine | 0.5 |
| "Complex" of liposomes in the atelocollagenglycosaminoglycan stabilizing support according to the invention | 30 |
| Purified water | 50.8 |
|  | 100% |

The preparation of this composition in emulsified form is carried out in the following manner.

First, an emulsion is prepared in purified water of all of the components, other than the "complex" of liposomes in the atelocollagenglycosaminoglycan stabilizing support according to the invention, in a standard manner.

Once this emulsion is formed, the "complex" of liposomes in the atelocollagen-glycosaminoglycan stabilizing support according to the invention, such as that prepared according to examples 1 or 2, with stirring which is maintained for 1 hour, care being taken to maintain the temperature below 30° C.

In this way, a composition in emulsified form is obtained in which liposomes are stable.

This stability was checked by electron microscopy and constitutes a remarkable result of the invention.

Naturally, the present invention comprises all of the agents constituting technical equivalents of the agents described as well as their various combinations. For example, it is quite clear that the term "glycosaminoglycan" need not be interpreted strictly and that it includes the mucopolysaccarides as equivalents, given that the glycosaminoglycans are polymers constituted of disaccharide units arranged in a linear manner and usually composed of an uronic acid and a hexosamine. Thus, the mucopolysaccharides are included in the definition of the glycosaminoglycans.

Similarly, the atelocollagen must be understood as being collagen from which the telopeptides have been removed and which constitute uncross-linked collagen as understood by the person skilled in the art.

Finally, it is to be observed that the combination according to the invention of glycosaminoglycans and atelocollagen makes it possible to prepare a stabilizing support in the form of a solution at a pH close to neutrality without precipitation of the atelocollagen being brought about. Furthermore, the support according to the invention makes it possible to prepare emulsions without difficulty; that constitutes one of the decisive technical advantages of the invention.

In addition, the glycosaminoglycans suppress almost completely the residual antigenicity of the atelocollagen.

It is also to be noted that the complete composition prepared according to the invention may be lyophilized, and this constitutes a crucial industrial advantage.

Finally, the liposome may be manufactured by any method of manufacture of the vesicles of the liposome type compatible with the introduction of the lipids in an atelocollagenglycosaminoglycan solution.

What is claimed is:

1. A composition containing liposomes wherein said liposomes are stabilized by the presence of a stabilizing support comprising a substantially homogeneous aqueous solution containing atelocollagen and glycosaminoglycans, the relative weight ratio of glycosaminoglycans with respect to atelocollagen ranging between 10 and 70 percent.

2. The composition of claim 1, wherein the liposomes are prepared in the presence of the stabilizing support.

3. The composition of claim 1, wherein the glycosaminoglycans used are selected from the group consisting of structural glycosaminoglycans and secretory glycosaminoglycans.

4. The composition of claim 3, wherein the structural glycosaminoglycans are selected from the group consisting of hyaluronic acid, chondroitin 4-sulfate, chondroitin 6-sulfate, dermatan sulfate, heparan sulfate, and keratan sulfate.

5. The composition of claim 3, wherein the secretory glycosaminoglycans are selected from the group consisting of heparin and the mucoitin sulfates.

6. The composition of claim 1, wherein the relative proportion of glycosaminoglycans with respect to atelocollagen varies from 18 to 25% by weight.

7. The composition of claim 1, wherein the solution of stabilizing support has a pH of about 8.

8. The composition of claim 1, wherein this composition is obtained by mixing substantially equal volumes of solution of liposomes, and solution(s) of the stabilizing support.

9. The composition of claim 1, wherein the said composition is in a lyophilized form.

10. A stabilization process for stabilizing liposomes comprising mixing said liposomes with a stabilizing support comprising a substantially homogenous mixture of atelocollagen and glycosaminoglycans in a relative weight ratio of glycosaminoglycans with respect to atelocollagen ranging between 10 and 70 percent.

11. The process of claim 10, wherein the concentration of glycosaminoglycans in the solution of glycosaminoglycans is in the range of about 0.5 to 4.

12. The process of claim 10, wherein the solution of atelocollagen is an aqueous solution of atelocollagen having a concentration in the range of about 0.5 and 2% by weight.

13. The process of claim 10, wherein the liposomes are prepared in the presence of the stabilizing support.

14. The process of claim 10, wherein the solution of atelocollagen is an aqueous solution of atelocollagen having a preferred concentration of about 1% by weight.

15. The process of claim 10, wherein the said stabilizing support is prepared in the following manner:
  (a) a solution of atelocollagen and a solution of glycosaminoglycans are prepared separately; then
  (b) the said atelocollagen solution is mixed with the solution of glycosaminoglycans.

16. The process of claim 15, wherein the mixture is prepared by introducing the solution of glycosaminoglycans into the solution of atelocollagen.

17. The process of claim 10, wherein the solution of glycosaminoglycans is prepared by dissolving the glycosaminoglycans in an aqueous solution, the pH of which is adjusted so that after mixing with the solution of atelocollagen, the pH of the mixture constituting the stabilizing support is of about 8.

18. The process of claim 17, wherein said aqueous solution is an aqueous solution of sodium hydroxide.

19. The process of claim 10, wherein the atelocollagen solution is prepared by dissolving atelocollagen fibres in a slightly acidic aqueous solution.

20. The process of claim 19, wherein the atelocollagen fibres are dissolved in 0.1M acetic acid.

21. The process of claim 15, wherein the atelocollagen is obtained by enzymatic digestion of collagen.

22. The process of claim 15, wherein the liposomes are introduced into the solution of the stabilizing support, the volumes of the two components being substantially equal.

23. The process of claim 22, wherein the proportion of the liposomes is about 1 percent by weight of the final composition.

24. A cosmetic composition comprising liposomes, which liposomes are stabilized by a stabilizing support comprising a substantially homogenous aqueous solution containing atelocollagen and glycosaminoglycans, the relative weight ratio of the glycosaminoglycans with respect to atelocollagen ranging between 10 and 70 percent; in a cosmetically acceptable excipient.

25. The cosmetic composition of claim 24, wherein said cosmetic composition is under lyophilized form.

26. The cosmetic composition of claim 24, wherein said cosmetic composition is in an emulsified form.

27. The cosmetic composition of claim 24, wherein said liposomes are encapsulating a cosmetic ingredient.

28. The cosmetic composition of claim 27, wherein said active ingredient is heparan sulfate.

* * * * *